(12) United States Patent
Peng et al.

(10) Patent No.: US 9,938,230 B2
(45) Date of Patent: Apr. 10, 2018

(54) ESTERS OR SALTS OF 2-HYDROXY-4-PROPYLCYCLOHEPTA-2,4,6-TRIENONE AND APPLICATION THEREOF IN PREPARATION OF ANIMAL ANTIBACTERIAL AGENTS AND GROWTH PROMOTERS USED IN FEED

(71) Applicant: GUANGZHOU INSIGHTER BIOTECHNOLOGY CO., LTD., Luogang, Guangzhou, Guangdong (CN)

(72) Inventors: Xianfeng Peng, Guangzhou (CN); Zonghua Qin, Guangzhou (CN); Fang Li, Guangzhou (CN); Jijun Huang, Guangzhou (CN); Xiaolan Ye, Guangzhou (CN); Zaolong Li, Guangzhou (CN)

(73) Assignee: GUANGZHOU INSIGHTER BIOTECHNOLOGY CO., LTD., Guangdong (CN)

( * ) Notice: Subject to any disclaimer, the term of this patent is extended or adjusted under 35 U.S.C. 154(b) by 17 days.

(21) Appl. No.: 15/110,512

(22) PCT Filed: Feb. 17, 2014

(86) PCT No.: PCT/CN2014/072126
§ 371 (c)(1),
(2) Date: Jul. 8, 2016

(87) PCT Pub. No.: WO2015/103806
PCT Pub. Date: Jul. 16, 2015

(65) Prior Publication Data
US 2016/0332954 A1    Nov. 17, 2016

(30) Foreign Application Priority Data
Jan. 10, 2014  (CN) .......................... 2014 1 0013396

(51) Int. Cl.
C07C 69/74 (2006.01)
C07C 69/24 (2006.01)
(Continued)

(52) U.S. Cl.
CPC ............ *C07C 69/74* (2013.01); *A23K 20/111* (2016.05); *A23K 20/195* (2016.05);
(Continued)

(58) Field of Classification Search
CPC ...... A23K 20/195; A23K 20/111; C07C 69/74
(Continued)

(56) References Cited

U.S. PATENT DOCUMENTS 4,547,365 A    10/1985    Kubo et al.
4,548,811 A    10/1985    Kubo et al.

FOREIGN PATENT DOCUMENTS

CN    100999451 A    7/2007
CN    101396021 A    4/2009
(Continued)

OTHER PUBLICATIONS

Okabe et al, "Antibacterial and preservative effects of natural Hinokitiol (b-Thujaplicin) extracted from wood," Acta Agriculturae Zhejiangensis, vol. 6(4), 1994, pp. 257-266.*
(Continued)

*Primary Examiner* — Craig D Ricci
*Assistant Examiner* — Janet L. Coppins
(74) *Attorney, Agent, or Firm* — Westerman, Hattori, Daniels & Adrian, LLP

(57) ABSTRACT

Esters or salts of 2-hydroxy-4-propyleyclohepta-2,4,6-trienone, and applications thereof in preparation of animal antibacterial agents and growth promoters used in feed. The esters or salts of 2-hydroxy-4-propylcyclohepta-2,4,6-trienone has a structural formula as shown in formula 1 or
(Continued)

2: in formula 1, R1 represents heptadecyl; and in formula 2, L is sodium, potassium, calcium, magnesium, zinc, copper or manganese. The esters or salts of 2-hydroxy-4-propyley-clohepta-2,4,6-trienone, as shown in formula 1 or 2, have high stability and safety, and good antibacterial and growth promotion effects, which make them preferable to be used as animal antibacterial agents and growth promoters in feed, and have a very good application prospect in the cultivation industry.

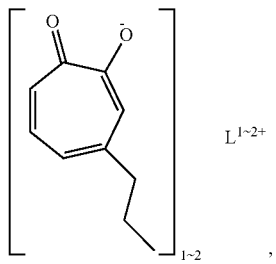

Formula 2

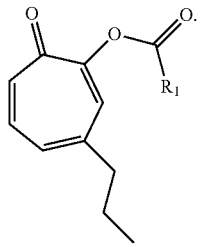

Formula 1

8 Claims, 1 Drawing Sheet

(51) Int. Cl.
C07C 49/717 (2006.01)
A23K 20/111 (2016.01)
A23K 20/195 (2016.01)

(52) U.S. Cl.
CPC .............. *C07C 49/717* (2013.01); *C07C 69/24* (2013.01); *C07C 2601/18* (2017.05)

(58) Field of Classification Search
USPC ........................................................ 514/522
See application file for complete search history.

(56) References Cited

FOREIGN PATENT DOCUMENTS

JP 7-33708 A 2/1995
JP 11-29408 A 2/1999
WO 2013/192554 A1 12/2013

OTHER PUBLICATIONS

Zhou et al., "Antibacterial Activity of Hinokitiol and Tropolone", Hubei Agricultural Sciences, Jun. 2012, vol. 51, No. 11, pp. 2230-2232 and 2273, w/English abstract (5 pages).
Okabe et al., "Antibacterial and preservative effects of natural Hinokitiol (β-Thujaplicin) extracted from wood", Acta Agriculturae Zhejiangensis, 6 (4), 1994, pp. 257-266, w/English abstract (11 pages).
International Search Report dated Nov. 26, 2014, issued in counterpart International Application No. PCT/CN2014/072126 (2 pages).

* cited by examiner

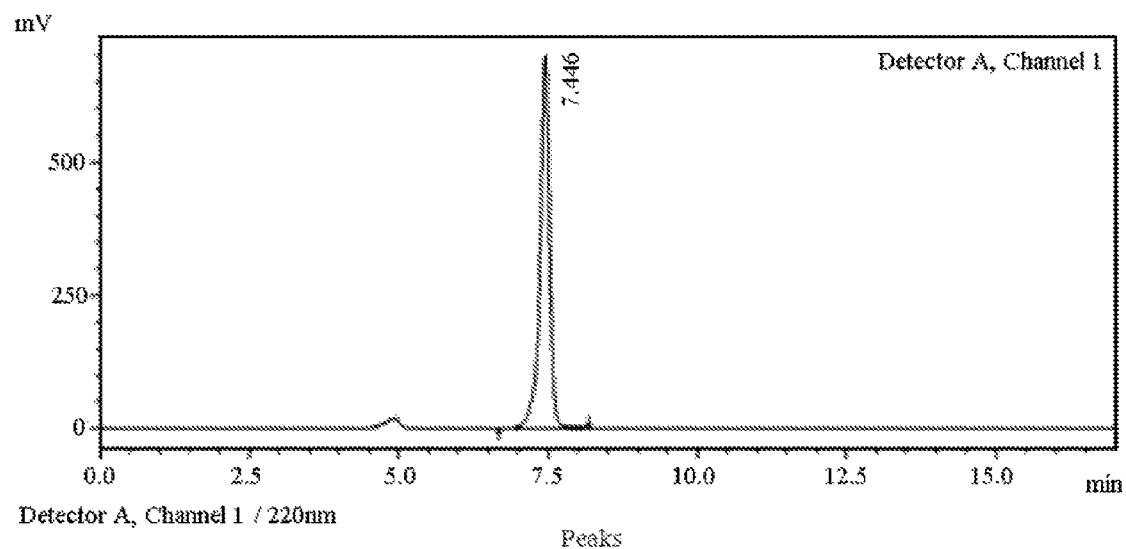

ESTERS OR SALTS OF 2-HYDROXY-4-PROPYLCYCLOHEPTA-2,4,6-TRIENONE AND APPLICATION THEREOF IN PREPARATION OF ANIMAL ANTIBACTERIAL AGENTS AND GROWTH PROMOTERS USED IN FEED

FIELD OF THE INVENTION

The present invention relates to the field of animal antibacterial agents and growth promoters used in feed, specifically to the esters or salts of 2-hydroxy-4-propylcyclohepta-2,4,6-trienone and applications thereof in preparation of animal antibacterial agents and growth promoters used in feed.

BACKGROUND OF THE INVENTION

As an active analogue of β-hinokitiol (also known as hinodiol, thujaplicin or 2-hydroxy-4-isopropyl-1-cyclohepta-2,4,6-trienone, which is a component of natural edible essential oil, and has been used as a food additive for years in Japan), 2-hydroxy-4-propylcyclohepta-2,4,6-trienone is researched and developed by Guangzhou Insighter Biotechnology Co., Ltd.

However, 2-hydroxy-4-propylcyclonepta-2,4,6-trienone (IST-009-001) has thermal instability and optical instability. To use 2-hydroxy-4-propylcyclohepta-2,4,6-trienone as a food additive, such problems must be solved.

SUMMARY OF THE INVENTION

The first object of the present invention is to provide esters or salts of 2-hydroxy-4-propylcyclohepta-2,4,6-trienone which are more stable, can promote the growth of livestock and are preferable to be used as feed additives and medical products.

The esters or salts of 2-hydroxy-4-propylcyclohepta-2,4,6-trienone of the present invention have a structural formula as shown in formula 1 or 2:

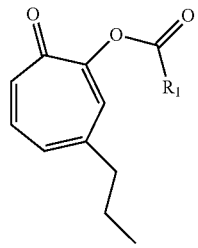

Formula 1: wherein, R1 represents heptadecyl:

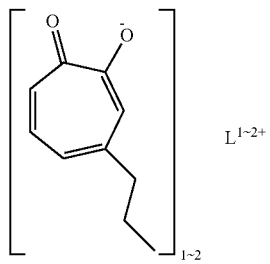

Formula 2: wherein, L is sodium, potassium, calcium, magnesium, zinc, copper or manganese.

Preferably, L is magnesium, zinc, copper or manganese.

The second object of the present invention is to provide application of the above-mentioned esters or salts of 2-hydroxy-4-propylcyclohepta-2,4,6-trienone in preparation of animal antibacterial agents and growth promoters used in feed.

The animals include pigs, chickens, ducks, geese, beef cattle, dairy cattle, sheep, fish, shrimps, foxes, martens or raccoon dogs in all growth stages.

Dosage of the esters or salts of 2-hydroxy-4-propylcyclohepta-2,4,6-trienone in animal feed is 0.1~200 ppm.

The animal feed can be complete formula feed.

The esters or salts of 2-hydroxy-4-propylcyclohepta-2,4,6-trienone of the present invention, as shown in formula 1 or 2, have high stability and safety, and good antibacterial and growth promotion effects to be preferable using as animal antibacterial agents and growth promoters in feed, and have a very good application prospect in the cultivation industry.

BRIEF DESCRIPTION OF THE DRAWINGS

FIG. 1 is an HPLC chromatogram of the manganese(II) 7-oxo-3-propylcyclohepta-1,3,5-trienolate in Embodiment 8.

DETAILED DESCRIPTION OF THE EMBODIMENTS

The present invention is described in further detail with reference to embodiments which shall not be regarded as limits in the present invention.

Embodiment 1

Structural Formula

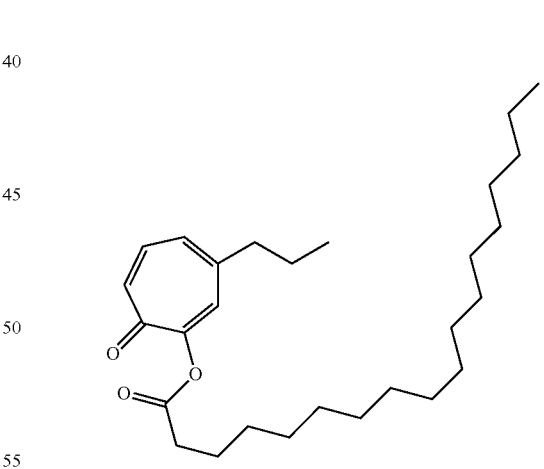

Preparation of 7-oxo-3-propylcyclohepta-1,3,5-trien-1-yl stearate (IST-009-050)

Preparation Process 2-hydroxy-4-propylcyclohepta-2,4,6-trienone (3.28 g, 20 mmol, 1 eq) and triethylamine (1~10 eq) were dissolved in 100 ml of dichloromethane; at −10° C.~25° C., to the resulting solution was added dropwise slowly with a mixture of n-octadecanoyl chloride (0.8~5 eq) and about 30 ml of dichloromethane. The resulting reaction mixture was stirred for 3-8 h. Thin layer chromatography (TLC, developing solvent: petroleum ether:ethyl acetate=5:1), in which a new spot appeared while an impurity spot appeared at the initial spot, showed that almost all the reactants were consumed. Then the resulting reaction solution was washed with 100 ml of water and then with saturated salt water, but fluorescence was still observed at the initial spot of TLC. The organic phase was then wash with dilute aqueous solution of potassium hydroxide, mixed with 8 g of silica gel, and separated over a silica column, wherein the eluent was a mixture of petroleum ether, ethyl acetate and triethylamine in a ratio of 5:1:0.02. A pure product (7-oxo-3-propylcyclohepta-1,3,5-trien-1-yl stearate) was obtained, with a purity of 98%.

7-oxo-3-propylcyclohepta-1,3,5-trien-1-yl stearate: δH (CDCl$_3$, 500 MHz) 7.068~7.102 (2H, m), 6.982~7.024 (1H, m), 6.879~6.899 (1H, d), 2.593~2.623 (2H, m), 2.493~2.523 (2H, m), 1.731~1.791 (2H, m), 1.606~1.681 (2H, m), 1.389~1.433 (2H, m), 1.256 (26H, m), 0.950~0.979 (3H, m), 0.869~0.890 (3H, m).

Embodiment 2

Structural Formula

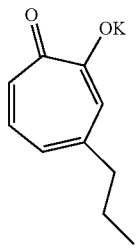

Preparation of potassium
7-oxo-3-propylcyclohepta-1,3,5-trienolate

Potassium hydroxide (1~3 eq) and 2-hydroxy-4-propyl-cyclohepta-2,4,6-trienone were dissolved in sequence in 150 ml of ethanol at room temperature, and the resulting solution was refluxed for 1-4 h and became clear, and was cooled to room temperature wherein no precipitate was observed. And then the solution was cooled to −40~−20V to give a great amount of precipitate which was collected by filtration. The filter cake was washed with cold ethanol and then subjected to rotary evaporation to give a product (potassium 7-oxo-3-propylcyclohepta-1,3,5-trienolate), a purity of which was 99% by HPLC.

Embodiment 3

Structural Formula

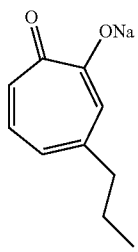

Preparation of sodium
7-oxo-3-propylcyclohepta-1,3,5-trienolate

Sodium hydroxide (1~5 eq) and 2-hydroxy-4-propylcy-clohepta-2,4,6-trienone were dissolved in sequence in 100 ml of ethanol at room temperature. The resulting solution was reflux for 1~5 h to (live precipitate, cooled to room temperature, stirred for 2 h, and then filtrated. The filter cake was washed with cold ethanol, and then subjected to rotary evaporation at 40° C. to give 15.9 g of product (sodium 7-oxo-3-propylcyclohepta-1,3,5-trienolate), a purity of which was 99% by HPLC.

Embodiment 4

Structural Formula

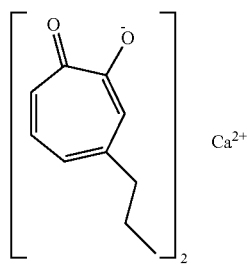

Preparation of calcium
7-oxo-3-propylcyclohepta-1,3,5-trienolate

Potassium hydroxide (1~5 eq) was dissolved in 300 ml of water at room temperature. Then the mixture was cooled to room temperature, added with 2-hydroxy-4-propylcyclo-hepta-2,4,6-trienone (16.4 g, 100 mmol, 1 eq), and stirred at room temperature until complete dissolution. To the resulting solution was added 80 ml of aqueous solution of calcium chloride (0.4~2 eq) dropwise to give a precipitate and the solution became viscous, then the solution was stirred for 2~3 h at room temperature, and subjected to suction filtration. Filter cake was washed with 200 ml of water twice, subjected to vacuum drying, and then dried in an oven at 35° C. to give a product (calcium 7-oxo-3-propylcyclohepta-1,3,5-trienolate), a purity of which was 99% by HPLC.

Embodiment 5

Structural Formula

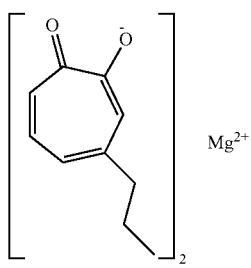

Preparation of magnesium 7-oxo-3-propylcyclohepta-1,3,5-trienolate

Potassium hydroxide (1~5 eq) was dissolved in 300 ml of water at room temperature. Then the mixture was cooled to room temperature, added with 2-hydroxy-4-propylcyclohepta-2,4,6-trienone (16.4 g, 100 mmol, 1 eq), and stirred at room temperature until complete dissolution. To the resulting solution was added 80 ml of aqueous solution of hexahydrated magnesium chloride (0.4~2 eq) dropwise to give a precipitate and the solution became viscous, then the solution was stirred for 2~3 h at room temperature, and subjected to suction filtration. Filter cake was washed with 200 ml of water twice, subjected to vacuum drying, and then dried in an oven at 35 to give a product (magnesium 7-oxo-3-propylcyclohepta-1,3,5-trienolate), a purity of which was 99% by HPLC.

Embodiment 6

Structural Formula

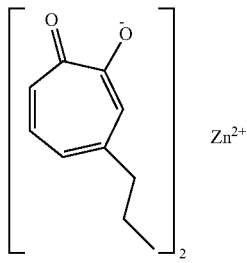

Preparation of zinc 7-oxo-3-propylcyclohepta-1,3,5-trienolate

Potassium hydroxide (1~5 eq) was dissolved in 300 ml of water at room temperature. Then the mixture was cooled to room temperature, added with 2-hydroxy-4-propylcyclohepta-2,4,6-trienone (16.4 g, 100 mmol, 1 eq), and stirred at room temperature until complete dissolution. To the resulting solution was added 100 ml of aqueous solution of zinc sulfate (0.4~2 eq) dropwise to give a precipitate and the solution became viscous, then the solution was stirred for 2~3 h at room temperature, and subjected to suction filtration. Filter cake was washed with 200 ml of water twice, subjected to vacuum drying, and then dried in an oven at 35° C. to give a product (zinc 7-oxo-3-propylcyclohepta-1,3,5-trienolate), a purity of which was 99% by HPLC.

Embodiment 7

Structural Formula

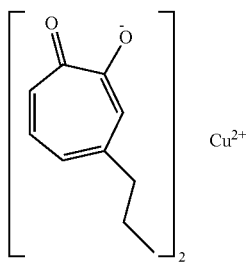

Preparation of copper 7-oxo-3-propylcyclohepta-1,3,5-trienolate

Potassium hydroxide (1~5 eq) was dissolved in 300 ml of water at room temperature. Then the mixture was cooled to room temperature, added with 2-hydroxy-4-propylcyclohepta-2,4,6-trienone (16.4 g, 100 mmol, 1 eq), and stirred at room temperature until complete dissolution. To the resulting solution was added 100 ml of aqueous solution of copper chloride (0.4~2 eq), dropwise to give a precipitate and the solution became viscous, then the solution was stirred for 2~3 h at room temperature, and subjected to suction filtration. Filter cake was washed with 200 ml of water twice, subjected to vacuum drying, and then dried in an oven at 35° C. to give a product (copper 7-oxo-3-propylcyclohepta-1,3,5-trienolate), a purity of which was 99% by HPLC.

Embodiment 8

Structural Formula

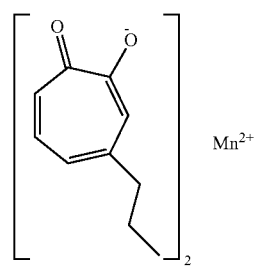

Preparation of manganese 7-oxo-3-propylcyclohepta-1,3,5-trienolate

Potassium hydroxide (1~5 eq) was dissolved in 300 ml of water at room temperature. Then the mixture was cooled to room temperature, added with 2-hydroxy-4-propylcyclohepta-2,4,6-trienone (16.4 g, 100 mmol, 1 eq), and stirred at room temperature until complete dissolution. To the resulting solution was added 100 ml of aqueous solution of manganese sulfate (0.4~2 eq) dropwise to give a precipitate and the solution became viscous, then the solution was stirred for 2~3 h at room temperature, and subjected to suction filtration. Filter cake was washed with 200 ml of water twice, subjected to vacuum drying, and then dried in an oven at 35° C. to give a product (manganese 7-oxo-3-propylcyclohepta-1,3,5-trienolate), a purity of which was 99% by HPLC.

Embodiment 9: Thermal Stability Test of 7-oxo-3-propylcyclohepta-1,3,5-trien-1-yl Stearate in High Temperature The prepared 7-oxo-3-propylcyclohepta-1,3,5-trien-1-yl stearate (IST-009-050) was mixed with corncob powder to obtain a premix with a mass fraction of 2%. Samples (the premix) were placed in crucibles and spread, and then placed in oven at 60° C. or eat for different durations. Then 1.0 g of each of the samples (three duplicate samples from each sample) and 50 ml of ethanol were added into a conical flask, subjected to sonication for 10 min, and then filtrated through filter paper. The filtrate was transferred into a 50 ml volumetric flask, topped up to the final volume with ethanol, and then filtered with a 0.45 μm microporous membrane and subjected to HPLC analysis.

Chromatographic Parameters

Column: Wondasil $C_{18}$ (250 mm×4.6 mm, 5 μm);

Mobile Phase: acetonitrile (100%);

Detection Wavelength: 220 nm;

Column Temperature: 25° C.;

Injection Volume: 20 μL;

Flow Rate: 0.8 or 1.0 ml/min.

Results of the stability test were as shown in table 1.

Results showed that the thermal stability of 7-oxo-3-propylcyclohepta-1,3,5-trien-1-yl stearate is better than the unesterified 2-hydroxy-4-propylcyclohepta-2,4,6-trienone (IST-009-001), but not satisfactory yet.

TABLE 1

Results of thermal stability test of 7-oxo-3-propylcyclohepta-1,3,5-trien-1-yl stearate

| Compound | Temperature (° C.) | Time (h) | Content (%) |
|---|---|---|---|
| IST-009-050 | — | — | 2.0 |
| IST-009-050 | 60 | 22 | 0.84 |
| IST-009-050 | 80 | 22 | 0.61 |
| IST-009-050 | 60 | 44 | 0.35 |
| IST-009-050 | 80 | 44 | 0.03 |
| IST-009-050 | 60 | 68 | 0.14 |
| IST-009-050 | 80 | 68 | 0 |
| IST-009-001 | 80 | 22 | 0 |
| IST-009-001 | 80 | 44 | 0 |
| IST-009-001 | 80 | 68 | 0 |

Embodiment 10: Thermal Stability Test of Different Metal Salts of 2-hydroxy-4-propylcyclohepta-2,4,6-trienone Each of the metal salts of 2-hydroxy-4-propylcyclohepta-2,4,6-trienone prepared in Embodiments 2-6 was mixed with corncob powder to obtain a premix with a mass fraction of 2%. Samples (the premix) were placed in crucibles and spread, and then placed in oven at 100° C. for different durations. Then 1.0 g of each of the samples (three duplicate samples from each sample) and 50 ml of ethanol were added into a conical flask, subjected to sonication for 10 min, and then filtrated through filter paper. The filtrate was transferred into a 50 ml volumetric flask, topped up to the final volume with ethanol, and then filtered with a 0.45 μm microporous membrane and subjected to HPLC analysis. Results of the thermal stability test were as shown in table 2.

Chromatographic Parameters

Column: Wondasil $C_{18}$ (250 mm×4.6 mm, 5 μm);

Mobile phase: methanol/40 mM ammonium acetate (65:35, v/v; pH 4):

Detection Wavelength: 220 nm;

Column Temperature: 25° C.;

Injection Volume: 20 μL;

Flow Rate: 0.8 or 1.0 ml/min.

Results showed that the thermal stability of the metal salts of IST-009-001 were all significantly enhanced in comparison with IST-009-001, wherein the magnesium, copper and manganese salts have the highest thermal stability.

TABLE 2

Results of thermal stability test of different metal salts of 2-hydroxy-4-propylcyclohepta-2,4,6-trienone

| Compound | Initial content (%) | Residual content at 100° C. for 20 h (%) | Residual content at 100° C. for 40 h (%) |
|---|---|---|---|
| Sodium 7-oxo-3-propylcyclohepta-1,3,5-trienolate | 2.0 | 1.31 | 1.11 |
| Potassium 7-oxo-3-propylcyclohepta-1,3,5-trienolate | 2.0 | 1.43 | 1.13 |
| Calcium 7-oxo-3-propylcyclohepta-1,3,5-trienolate | 2.0 | 1.73 | 1.67 |
| Magnesium 7-oxo-3-propylcyclohepta-1,3,5-trienolate | 2.0 | 1.99 | 1.99 |
| Zinc 7-oxo-3-propylcyclohepta-1,3,5-trienolate | 2.0 | 1.85 | 1.83 |
| 2-hydroxy-4-propylcyclohepta-2,4,6-trienone | 2.0 | 0 | 0 |
| Copper 7-oxo-3-propylcyclohepta-1,3,5-trienolate | 2.0 | 1.99 | 1.98 |
| Manganese 7-oxo-3-propylcyclohepta-1,3,5-trienolate | 2.0 | 1.99 | 1.98 |

Embodiment 11: Optical Stability Test of Different Metal Salts of 2-hydroxy-4-propylcyclohepta-2,4,6-trienone Each of the metal salts of 2-hydroxy-4-propylcyclohepta-2,4,6-trienone prepared in Embodiments 2-6 was mixed with corncob powder to obtain a premix with a mass fraction of 2%. Samples (the premixes) were spread in a stability test chamber and subjected to illumination at 4500-5000 lux for 5 days. Then 1.0 g of each of the samples (three duplicate samples from each sample) and 50 ml of ethanol were added into a conical flask, subjected to sonication for 10 min, and then filtrated through filter paper. The filtrate was transferred into a 50 ml volumetric flask, topped up to the final volume with ethanol, and then filtered with a 0.45 μm microporous membrane and subjected to HPLC analysis.

Column: Wondasil $C_{18}$ (250 mm×4.6 mm, 5 μm);

Mobile Phase: methanol/40 mM ammonium acetate (65:35, v/v; pH 4):

Detection Wavelength: 220 nm;

Column Temperature: 25° C.;

Injection Volume: 20 μL;

Flow Rate: 0.8 or 1.0 ml/min.

Results of the stability test were as shown in table 3. The results showed that the optical stability of the salts was enhanced, wherein results of the manganese, copper, zinc and magnesium salts were most significant.

TABLE 3

Optical stability of different metal salts of 2-hydroxy-4-propylcyclohepta-2,4,6-trienone

| Compound | Initial content (%) | Residual content of 5 days later (%) |
|---|---|---|
| Sodium 7-oxo-3-propylcyclohepta-1,3,5-trienolate | 2.0 | 0.05 |
| Potassium 7-oxo-3-propylcyclohepta-1,3,5-trienolate | 2.0 | 0.17 |
| Calcium 7-oxo-3-propylcyclohepta-1,3,5-trienolate | 2.0 | 0.89 |
| Magnesium 7-oxo-3-propylcyclohepta-1,3,5-trienolate | 2.0 | 1.52 |

TABLE 3-continued

Optical stability of different metal salts of 2-hydroxy-4-propylcyclohepta-2,4,6-trienone

| Compound | Initial content (%) | Residual content of 5 days later (%) |
|---|---|---|
| Zinc 7-oxo-3-propylcyclohepta-1,3,5-trienolate | 2.0 | 1.77 |
| IST-009-001 (2-hydroxy-4-propylcyclohepta-2,4,6-trienone) | 2.0 | 0 |
| Copper 7-oxo-3-propylcyclohepta-1,3,5-trienolate | 2.0 | 1.9 |
| Manganese 7-oxo-3-propylcyclohepta-1,3,5-trienolate | 2.0 | 1.96 |

Embodiment 12: Applications of Magnesium 7-oxo-3-propylcyclohepta-1,3,5-trienolate in Broiler Feeds 500 1-day-aged, healthy, fast-grown yellow feather broilers (female) in the same growing state and similar in weight were randomly divided into five groups according to table 4, 100 broilers in each group. Broilers of each group were fed with different dosages of magnesium 7-oxo-3-propylcyclohepta-1,3,5-trienolate or 2-hydroxy-4-propylcyclohepta-2,4,6-trienone. The broilers were kept in cages and fed with food and water ad libitum during a 30 days test period, wherein weight gain and feed conversion efficiency of the broilers fed with magnesium 7-oxo-3-propylcyclohepta-1,3,5-trienolate had been significantly improved.

TABLE 4

Grouping of tested animals, and dosage of additives

| Group | Quantity of the broilers | Additives | Dosage (ppm) | Administration |
|---|---|---|---|---|
| 1 | 100 | Blank Control | — | Mixed with feed |
| 2 | 100 | Magnesium 7-oxo-3-propylcyclohepta-1,3,5-trienolate | 2.5 | Mixed with feed |
| 3 | 100 | Magnesium 7-oxo-3-propylcyclohepta-1,3,5-trienolate | 5.0 | Mixed with feed |
| 4 | 100 | 2-hydroxy-4-propylcyclohepta-2,4,6-trienone | 2.5 | Mixed with feed |
| 5 | 100 | 2-hydroxy-4-propylcyclohepta-2,4,6-trienone | 5.0 | Mixed with feed |

TABLE 5

Application effects of magnesium 7-oxo-3-propylcyclohepta-1,3,5-trienolate in broiler feeds

| Group | Initial weight (g) | Average weight gain (g) | Consumption (kg) | Average daily weight gain (g) | Feed conversion efficiency |
|---|---|---|---|---|---|
| 1 | 41.03 | 735 | 151.78 | 24.5 | 2.065 |
| 2 | 41.24 | 785 | 155.94 | 26.2 | 1.984 |
| 3 | 42.47 | 798 | 151.54 | 26.6 | 1.899 |
| 4 | 42.62 | 783 | 156.66 | 26.1 | 1.988 |
| 5 | 41.18 | 804 | 153.24 | 26.8 | 1.906 |

The invention claimed is:

1. A compound which is an ester of 2-hydroxy-4-propylcyclohepta-2,4,6-trienone, according to the following structural formula 1:

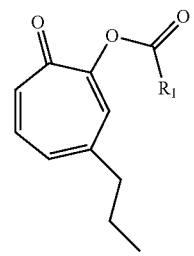

wherein, R1 represents heptadecyl; or
a compound which is a salt of 2-hydroxy-4-propylcyclohepta-2,4,6-trienone, according to the following structural formula 2:

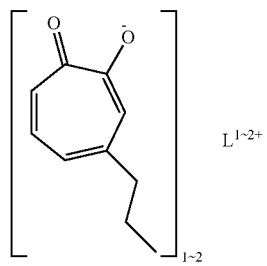

wherein, L is sodium, potassium, calcium, magnesium, zinc, copper or manganese.

2. The compound according to claim 1, wherein L is magnesium, zinc, copper or manganese.

3. A feed additive containing an animal antibacterial agent, comprising the compound of claim 1.

4. The feed additive according to claim 3, wherein said animal includes pigs, chickens, ducks, geese, beef cattle, dairy cattle, sheep, fish, shrimp, foxes, martens or raccoon dogs in all growth stages.

5. The feed additive according to claim 3, wherein a dosage of the compound in animal feed is 0.1~200 ppm.

6. A feed additive containing a growth promoter, comprising the compound of claim 1.

7. The feed additive according to claim 6, wherein said animal includes pigs, chickens, ducks, geese, beef cattle, dairy cattle, sheep, fish, shrimp, foxes, martens or raccoon dogs in all growth stages.

8. The feed additive according to claim 6, wherein a dosage of the growth promoter in the animal feed is 0.1~200 ppm.

* * * * *